Figure 1:
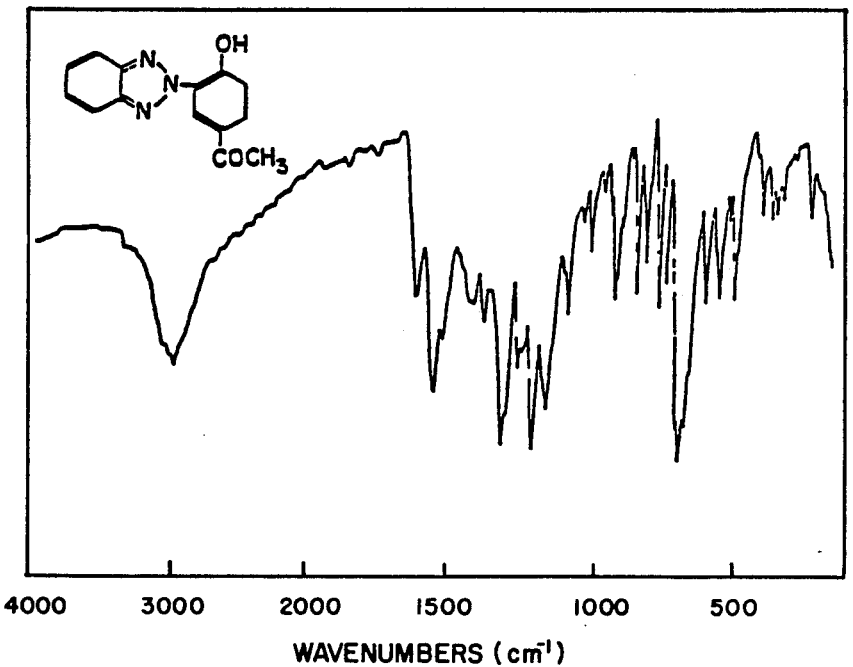

United States Patent [19]

Vogl et al.

[11] Patent Number: 4,812,575

[45] Date of Patent: Mar. 14, 1989

[54] PROCESS FOR THE PREPARATION OF BENOZOTRIAZOLES AND THEIR POLYMERS, AND 2(2-HYDROXY-5-ISOPROPENYL-PHENYL)2H-BENZOTRIAZOLE PRODUCED THEREBY

[75] Inventors: Otto Vogl, Brooklyn, N.Y.; Zohar Nir, Beer Sheva, Israel

[73] Assignee: The United States of America as represented by the United States Department of Energy, Washington, D.C.

[21] Appl. No.: 537,219

[22] Filed: Sep. 29, 1983

[51] Int. Cl.$^4$ ............................................. C07D 249/20
[52] U.S. Cl. ..................................... 548/260; 548/261
[58] Field of Search ....................... 548/259, 260, 261

[56] References Cited

U.S. PATENT DOCUMENTS

| | | | |
|---|---|---|---|
| 3,629,191 | 12/1971 | Heller et al. | 548/259 |
| 4,129,521 | 12/1978 | Strobel | 548/260 |

FOREIGN PATENT DOCUMENTS

| | | | |
|---|---|---|---|
| 1116230 | 11/1961 | Fed. Rep. of Germany | 548/260 |
| 2413005 | 10/1975 | Fed. Rep. of Germany | 548/261 |

OTHER PUBLICATIONS

Pradellok, et al., "Functional Polymers . . . ,", Chem. Abst. 96: 52824y (1961).
Yoshida et al., "Functional Polymers, . . . " Chem. Abst. 96: 143359s (1982).
Nir, et al., "Functional Polymers . . . ," Chem. Abst. 97: 126753y (1982).
Meislich, et al., Schaum's Outline of Organic Chemistry, McGraw-Hill, New York (1977), pp. 229, 230.
Deshchits et al., "Study of . . . Methanol Dehydration", Chem. Abst. 88: 121403(j), (1978).
Volkotrub et al., "Spectroscopic Characteristics and Efficiency of Light Stabilizers . . . ", Chem. Abst. 84: 151415z (1976).

Primary Examiner—Donald G. Daus
Assistant Examiner—Mark W. Noel
Attorney, Agent, or Firm—William W. Randolph; Judson R. Hightower; Richard E. Constant

[57] ABSTRACT

The compound 2(2-hydroxy-5-isopropenylphenyl)2H-benzotriazole (2H5P) is produced by azo coupling of o-nitrophenyl diazonium chloride with p-hydroxyacetophenone, subjecting the resulting isolated azo compound to reductive cyclization with zinc in the presence of sodium hydroxide at a temperature of about 50°-70° C., acidifying the resulting mixture so as to produce (2(2-hydroxy-5-acetylphenyl)2H-benzotriazole (2H5A), acetylating the isolated 2(2-hydroxy-5-acetylphenyl)2H-benzotriazole (2H5A), so as to produce 2(2-acetoxy-5-acetylphenyl)2H-benzotriazole (2A5A), methylating the isolated 2(2-acetoxy-5-acetylphenyl(2H-benzotriazole (2A5A) with a methyl Grignard reagent and dehydrating the isolated reaction product with potassium hydrogen sulfate so as to produce 2(2-hydroxy-5-isopropenylphenyl)2H-benzotriazole (2H5P). The compound is used as a polymerizable ultra violet light stabilizer.

2 Claims, 3 Drawing Sheets

IR Spectrum of 2(Hydroxy-5-Acetylphenyl)2H-Benzotriazole (2H5A)

IR Spectrum of 2(2-Hydroxy-5-Isopropenylphenyl)2H-Benzotriazole (2H5P)

CHEMICAL SHIFT, ppm $^1$H NMR Spectrum of 2(2-Hydroxy-5-Acetylphenyl)2H-Benzotriazole (2H5A)

CHEMICAL SHIFT, ppm $^1$H NMR Spectrum of 2(2-Hydroxy-5-Isopropenylphenyl)2H-Benzotriazole (2H5P)

$^{13}$C NMR Spectrum of 2(2-Hydroxy-5-Acetylphenyl)2H-Benzotriazole (2H5A)

$^{13}$C NMR Spectrum of 2(2-Hydroxy-5-Isopropenylphenyl)2H-Benzotriazole (2H5P)

PROCESS FOR THE PREPARATION OF BENOZOTRIAZOLES AND THEIR POLYMERS, AND 2(2-HYDROXY-5-ISOPROPENYLPHENYL)2H-BENZOTRIAZOLE PRODUCED THEREBY

The U.S. Government has rights to this invention pursuant to a U.S. Department of Energy funded N.A.S.A. contract NAS 7-100 with the University of Massachusetts.

This invention relates to a process for the production of substituted benzotriazoles, particularly for the production of such substituted benzotriazoles which are useful as polymerizable ultraviolet light absorbers. The invention also relates to a new benzotriazole, 2(2-hydroxy-5-isopropenylphenyl)2H-benzotriazole, which is a polymerizable ultraviolet light absorber, and its preparation, and to the preparation of 2(2-hydroxy-5-vinylphenyl)2H-benzotriazole, another polymerizable ultraviolet light absorber.

BACKGROUND

Increased attention has been directed recently to the preparation of polymerizable ultraviolet stabilizers, and many classical ultraviolet absorbing groups have been made into polymerizable ultraviolet stabilizers. However, derivatives of 2(2-hydroxyphenyl)2H-benzotriazoles seem to have the greatest utility because of the superior efficiency of 2(2-hydroxyphenyl)2H-benzotriazole as an ultraviolet absorbing group.

Attention has been focused on the synthesis of polymerizable ultraviolet stabilizers of the 2(2-hydroxyphenyl)-2H-benzotriazole family which are styrene derivatives—that is, compounds where a polymerizable vinyl group is attached directly to the phenyl ring of the 2(2-hydroxyphenyl)2H-benzotriazole system.

Recently, the synthesis of several benzotriazoles has been reported, specifically 2(2-hydroxy-5-vinylphenyl)2H-benzotriazole and 2(2-hydroxy-5-methylphenyl)5-vinyl-2H-benzotriazole. *Polymer Preprints,* ACS Division of Polymer Chemistry, 21(1), 201 (1980), S. Yoshida and O. Vogl,; *Rev. Roum. de Chemie,* O. Vogl and S. Yoshida, 25(7), 1128 (1980); *Makromol. Chem.,* S. Yoshida and O. Vogl, 183, 259 (1982); *J. Polym. Sci., Polymer Chem. Ed.,* S. Yoshida, et al. This work has resulted in the synthesis of polymeric, non-volatile and non-leachable ultraviolet stabilizers, and was part of a general effort to produce 2(2-hydroxyphenyl)2H-benzotriazole type ultraviolet stabilizers of high molecular weight.

Other work to increase the molecular weight of benzotriazole compounds has led to the synthesis of 4[[(2H-benzotriazole-2-yl)2,6-dimethylphenoxy]methyl]benzylidene malononitrile which has also been reported to be an effective ultraviolet stabilizer, in U.S. Pat. No. 4,070,337 (1980).

The introduction of polymerizable vinyl groups into ultraviolet absorbing molecules can be accomplished in several ways. Previous attempts to introduce vinyl groups into aromatic systems were made by brominating ethyl substituents with N-bromosuccinimide and subsequently dehydrobrominating the 1-bromoethyl compound to the vinyl compound.

Another technique has been reported for the synthesis of methyl 5-vinylsalicylate by reducing the acetyl compound with sodium borohydride followed by dehydration of the 1-hydroxyethyl compound with potassium hydrogen sulfate. However attempts to introduce an acetyl group into the 2(2-hydroxyphenyl)2H-benzotriazole system to accomplish a simple and direct synthesis of polymerizable vinyl 2(2-hydroxyphenyl)2H-benzotriazole were unsuccessful.

Because of the growing importance of, and interest in ultraviolet stabilizers, much work has continued in order to develop viable syntheses for such compounds.

OBJECTS AND SUMMARY OF THE INVENTION

A primary object of this invention is to provide an improved process for synthesizing benzotriazole ultraviolet light stabilizers.

Another object of this invenion is to provide new ultraviolet light stabilizers of the benzotriazole type.

Still another object of the present invention is to provide 2(2-hydroxy-5-isopropenylphenyl)2H-benzotriazole (2H5P) which is a novel ultraviolet light stabilizer.

A further object of this invention is to carry out the condensation of o-nitrophenyl diazonium chloride with p-hydroxyacetophenone, and to ring-close the azo compound to 2(2-hydroxy-5-acetylphenyl)2H-benzotriazole (2H5A), which is a key intermediate for the preparation of 2(2-hydroxy-5-isopropenylphenyl)2H-benzotriazole (2H5P) and 2(2-hydroxy-5-vinylphenyl)2H-benzotriazole (2H5V).

The process according to the invention comprises the azo coupling of o-nitrophenyl diazonium chloride with p-hydroxyphenone, followed by a reductive cyclization step with zinc in the presence of sodium hydroxide at a temperature of about 50°–70° C. Subsequent acidification of the solution produces 2(2-hydroxy-5-acetylphenyl)2H-benzotriazole (2H5A) which is a key intermediate, and which may then be further reacted (1) by reduction, dehydration, and hydrolysis, or (2) by a Grignard reaction, in order to produce the desired products.

The 2(2-hydroxy-5-acetylphenyl)2H-benzotriazole (2H5A) thus produced may then be (1) reduced with sodium borohydride followed by dehydration with potassium hydrogen sulfate to produce 2(2-hydroxy-5-vinylphenyl)2H-benzotriazole (2H5V), or (2) reacted with a methyl Grignard reagent and dehydrated with potassium hydrogen sulfate to produce 2(2-hydroxy-5-isopropenylphenyl)2H-benzotriazole (2H5P).

The 2-(2-hydroxy-5-isopropenylphenyl)2H-benzotriazole (2H5P) is a new polymerizable ultraviolet light stabilizer.

The 2H5V prepared according to this invention is a monomer which is free of bromine-containing impurities. Such impurities have been a serious problem in prior art attempts to synthesize 2H5V, since the presence of bromo compounds in the monomer gives rise to possible chain transfer reactions in polymerizations and consequently limits the molecular weight of polymers and copolymers.

According to the invention, 2(2-hydroxy-5-isopropenylphenyl)2H-benzotriazole (2H5P) was synthesized in a sequence of five steps with an overall yield of 40%, and its copolymerization was successfully accomplished. The synthesis according to the invention provides a key intermediate, 2(2-hydroxy-5-acetylphenyl)2H-benzotriazole (2H5A), which was successfully used to synthesize 2(2-hydroxy-5-vinylphenyl)-2H-benzotriazole (2H5V) by the new and improved method.

The synthesis of 2(2-hydroxy-5-acetylphenyl)2H-benzotriazole (2H5A) requires azo coupling of o-nitrophenyl diazonium chloride in concentrated hydrochloric acid solution at about 0° C. with p-hydroxyacetophenone.

The crude reaction product 2(2-hydroxy-5-acetylphenyl)2H-benzotriazole (2H5A) is then o-acetylated with an acetic anhydride/pyridine mixture, and after reflux, 2(2-acetoxy-5-acetylphenyl)2H-benzotriazole (2A5A) was produced. The 2(2-acetoxy-5-acetylphenyl)2H-benzotriazole (2A5A) is a key intermediate in the process, and in purified form served as the starting material for the two carbinols.

Grignard methylation of the 2(2-acetoxy-5-acetylphenyl)2H-benzotriazole (2A5A) produces 2[2-hydroxy-5-(2-hydroxy-2-propyl)phenyl]2H-benzotriazole (2H5PR) in 85–90% yield. Subsequent dehydration of the 2[2-hydroxy-5-(2-hydroxy-2-propyl)phenyl]2H-benzotriazole (2H5PR) produced 2(2-hydroxy-5-isopropenylphenyl)2H-benzotriazole (2H5P) which is a stable monomer which can be distilled and stored with no special precautions, and which can also be recrystallized from n-hexane or methanol, or can be sublimed.

Sodium borohydride reduction of 2(2-acetoxy-5-acetylphenyl)2H-benzotriazole (2A5A) produces a mixture of 2[2-hydroxy-5-(1-hydroxyethyl)phenyl]2H-benzotriazole (2H5HE) and 2[2-acetoxy-5-(1-hydroxyethyl)phenyl]2H-benzotriazole (2A5HE) in high yields and in a ratio of about 4:1. Dehydration of the mixture in the presence of picric acid (to prevent polymerization) with potassium hydrogen sulfate produces a mixture of 2(2-hydroxy-5-vinylphenyl)2H-benzotriazole (2H5V) and 2(2-acetoxy-5-vinylphenyl)2H-benzotriazole (2A5V) which is then hydrolyzed with sodium bicarbonate to 2(2-hydroxy-5-vinylphenyl)2H-benzotriazole (2H5V). This process proceeds in an overall yield of 85–90%.

Figure 2:
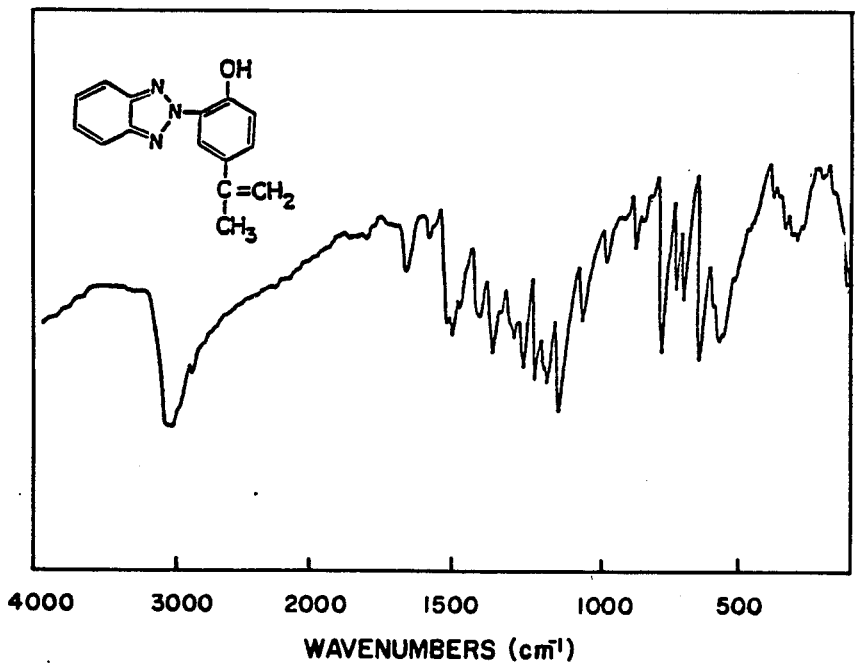
Figure 3:
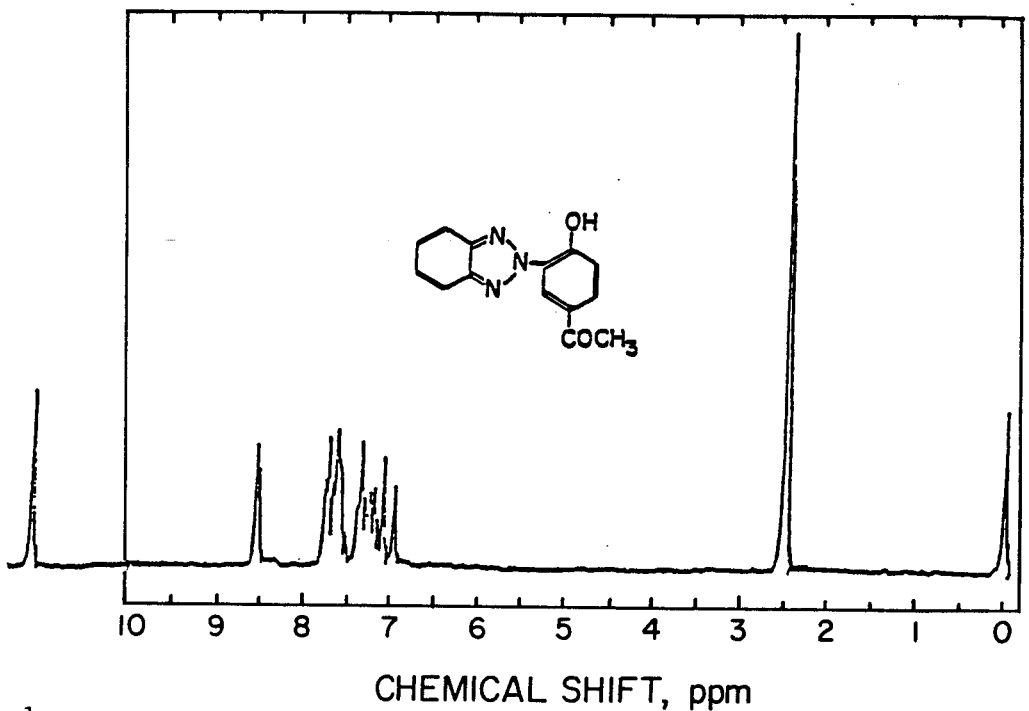
Figure 4:
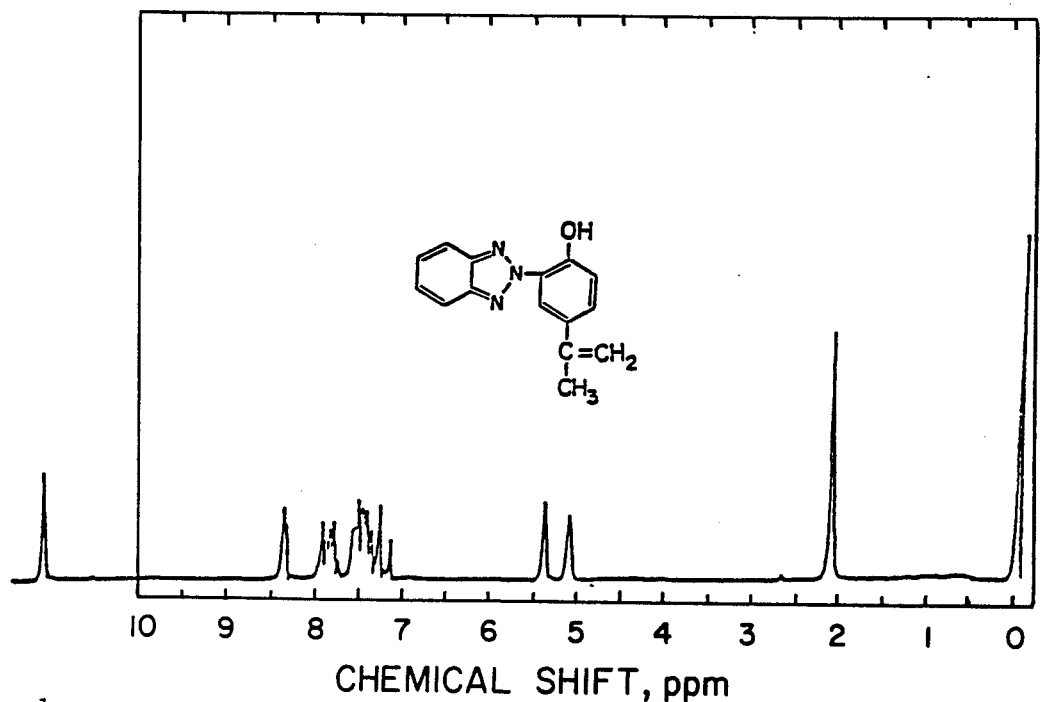
Figure 5:
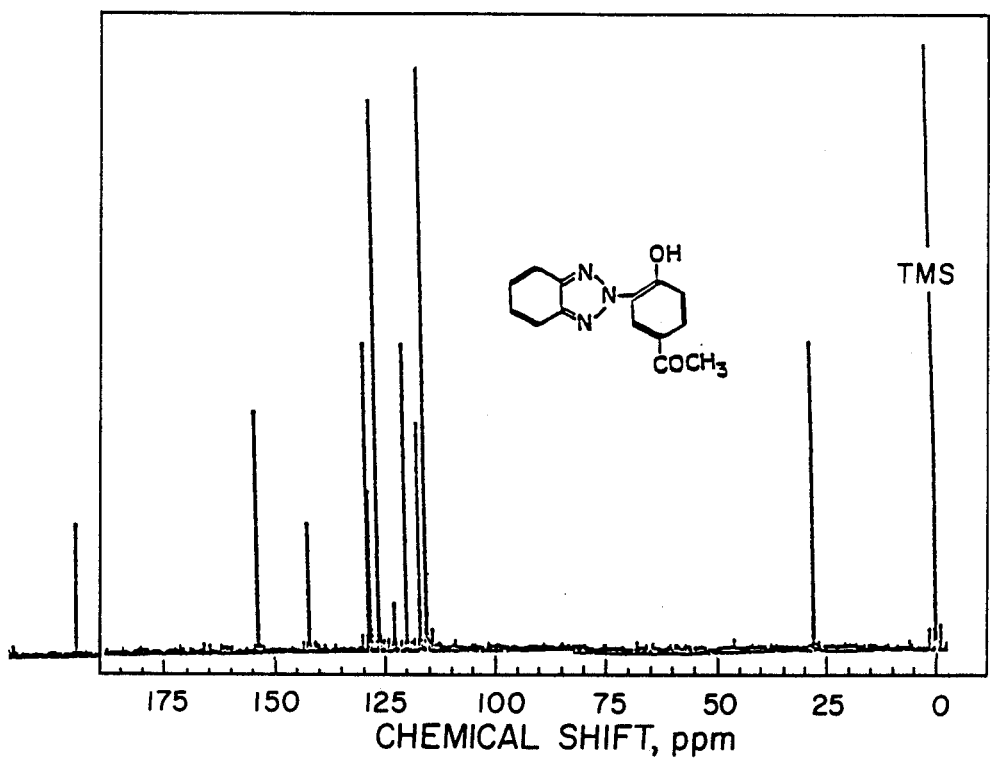
Figure 6:
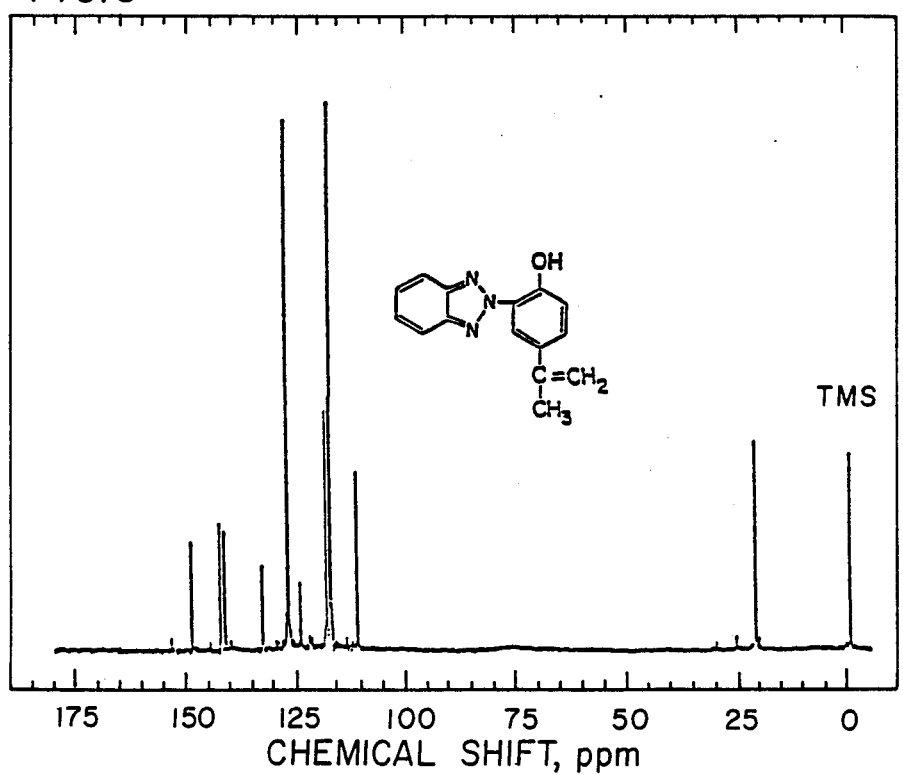

All of the intermediates were characterized by elemental analysis, infrared, $^1H$ and $^{13}C$ NMR spectra, and the infrared spectra for 2H5A and 2H5P are shown in FIGS. 1 and 2, the $^1H$ NMR spectra for 2H5A and 2H5P are shown in FIGS. 3 and 4, and the $^{13}C$ NMR spectra for 2H5A and 2H5P are shown in FIGS. 5 and 6.

The polymerization and grafting of 2(2-hydroxy-5-vinylphenyl)2H-benzotriazole (2H5V), and the polymerization, copolymerization and grafting of 2(2-hydroxy-5-isopropenylphenyl)2H-benzotriazole (2H5P) under conditions excluding oxygen were attempted. The results of the copolymerization of 2(2-hydroxy-5-isopropenylphenyl)2H-benzotriazole (2H5P) with methyl methacrylate, n-butyl acrylate and styrene are summarized in Table I.

Attempts to homopolymerize 2(2-hydroxy-5-isopropenylphenyl)2H-benzotriazole (2H5P) in toluene solutions with azobisisobutyronitrile (AIBN) as the initiator were unsuccessful, while under similar conditions, homopolymerization of 2(2-hydroxy-5-vinylphenyl)2H-benzotriazole (2H5V) readily occurs. This is the most important difference between the two monomers 2(2-hydroxy-5-isopropenylphenyl)2H-benzotriazole (2H5P) and 2(2-hydroxy-5-vinylphenyl)2H-benzotriazole (2H5V).

The 2(2-hydroxy-5-isopropenylphenyl)2H-benzotriazole (2H5P) was successfully copolymerized with methyl methacrylate and n-butylacrylate, and the relative amount of 2(2-hydroxy-5-isopropenylphenyl)2H-benzotriazole (2H5P) incorporated into the polymers was greater that its concentration in the monomer feed. Styrene monomer was used as its own solvent for copolymerization with 2(2-hydroxy-5-isopropenylphenyl)2H-benzotriazole (2H5P) which was readily incorporated into the copolymer.

Thus, 2-(2-hydroxy-5-isopropenylphenyl)2H-benzotriazole (2H5P) was synthesized as a new polymerizable ultraviolet absober. It is more stable than the vinyl compound toward polymerization, and while it does not homopolymerize to higher polymers, it readily copolymerizes with conventional resonance stabilized comonomers. This characteristic is substantially different from the characteristics of 2(2-hydroxy-5-vinylphenyl)2H-benzotriazole (2H5V) which readily homopolymerizes and has to be stabilized with radical inhibitors to prevent its polymerization even at normal temperatures.

The following examples show in greater detail the reactions and methods used for the preparation of the 2(2-hydroxy-5-isopropenylphenyl)2H-benzotriazole (2H5P) and 2(2-hydroxy-5-vinylphenyl)2H-benzotriazole (2H5V).

The following examples illustrate the invention in greater detail.

EXAMPLE 1

Preparation of 2(2-hydroxy-5-acetylphenyl)2H-benzotriazole (2H5A)

The synthesis of the first intermediate 2(2-hydroxy-5-acetylphenyl)2H-benzotriazole (2H5A) required azo coupling of o-nitrophenyl diazonium chloride in hydrochloric acid at 0° C. with p-hydroxyacetophenone. The p-hydroxyacetophenone was dissolved in sodium hydroxide solution, an excess of sodium carbonate was added and the solution cooled below 20° C.

The diazonium salt solution was prepared by rapidly quenching a warm solution of o-nitroaniline in concentrated hydrochloric acid to 0° C. with vigorous stirring, followed by dropwise addition of a solution of sodium nitrite (30 g, 0.45 mole) in water (100 ml) over a period of one hour at 0°–5° C., with care being taken to avoid excess sodium nitrite addition. The cold diazonium salt solution was added slowly to a solution of p-hydroxyacetophenone (55 g, 0.4 mole), sodium hydroxide (16 g, 0.4 mole) and sodium carbonate (120 g, 1.13 mole) in 600 ml of water over a period of 30 minutes through a dropping funnel which resulted in a deep red color formation and precipitation of a crystalline material.

After 2 hours, the azo compound was isolated in a yield of 90–95%.

The azo compound was redissolved in excess sodium hydroxide solution (25 weight percent in water) and the reductive cyclization to 2(2-hydroxy-5-acetylphenyl)2H-benzotriazole (2H5A) was carried out with zinc powder as described for the reduction of o-nitrophenyl azophenol in *Makromol. Chem.*, Vol. 183, P. 259, S. Yoshida and O. Vogl, (1982), which is incorporated herein by reference.

It was necessary that the reaction temperature for cyclization be kept between 50° and 70° C. for at least 4 hours, and after about 40 minutes, the suspension color changed from red to green, indicating that most of the azo compound had been consumed. The suspension was then decanted and the residue extracted twice (100 ml, 10% aqueous NaOH), and the combined solution was cooled to 5°–10° C. and acidified to pH 2 with concentrated hydrochloric acid. The creamy precipitate was filtered, dried at 0.05 mm, and produced 50 g (55% yield) of crude 2(2-hydroxy-5-acetylphenyl)2H-benzotriazole (2H5A). Recrystallization from MeOH gave white needles, m.p. 147° C.

Analysis calculated for $C_{14}H_{11}N_3O_2$ was: C 66.39%, H 4.38%, N 16.59%.

Analysis of the compound produced was: C 66.22%, H 4.18%, N 16.74%.

The cyclization of the corresponding azo compound to 2(2-hydroxy-5-acetylphenyl)2H-benzotriazole (2H5A) was also carried out with sodium dithionite, but this reductive cyclization was more difficult to carry out than the zinc/sodium hydroxide reduction and gave lower yields.

EXAMPLE 2

Preparation of 2(2-acetoxy-5-acetylphenyl)2H-benzotriazole (2A5A)

Crude 2(2-hydroxy-5-acetylphenyl)2H-benzotriazole (2H5A) (47 g, 0.18 mole) from Example 1 was acetylated at reflux temperature for 4 hours with acetic anhydride (115 g, 1.06 mole) in the presence of pyridine (14.6 g, 0.18 mole). The reaction mixture was cooled to room temperature and poured into a slurry of ice and water. The solid precipitate (crude 2(2-acetoxy-5-acetylphenyl)2H-benzotriazole 2A5A) was collected, air dried, recrystallized from methanol, and yielded 55 g (99%) of pale brown needles, m.p. 118°–119° C.

The analysis calculated for $C_{16}H_{13}N_3O_3$ was: C 65.07%, H 4.39%, N 14.23%.

The analysis found for the compound produced was: C 64.87%, H 4.36%, N 14.30%.

The overall yield from o-nitroaniline to 2(2-acetoxy-5-acetylphenyl)2H-benzotriazole (2A5A) was 45–50%. The 2(2-acetoxy-5-acetylphenyl)2H-benzotriazole (2A5A) is the key intermediate for the synthesis of the desired monomers.

EXAMPLE 3

Preparation of (2H5PR) 2[2-hydroxy-5-(2-hydroxy-2-propyl)phenyl]2H-benzotriazole 2[2-hydroxy-5-(2-hydroxy-2-propyl)phenyl]2H-benzotriazole (2H5PR) is prepared by the Grignard methylation of 2(2-acetoxy-5-acetylphenyl)2H-benzotriazole (2A5A) at a yield of about 85–90%.

In order to prepare the Grignard reagent, dry nitrogen was passed at a constant rate into a two liter, three neck flask, equipped with a mechanical stirrer, reflux condenser, and a pressure equalizing dropping funnel. Dry magnesium turnings (10.8 g, 0.45 moles), 200 ml of anhydrous diethyl ether and a small crystal of iodine were added and the stirrer started. Methyl iodide (64 g, 0.45 mole) was dissolved in anhydrous diethyl ether (50 ml) and the solution was added slowly from the dropping funnel into the stirred mixture.

The reaction started spontaneously, and methyl iodide was added at a rate such that the solution refluxed gently. The addition was made over a two hour period and the solution was stirred for an additional two hours; the methyl magnesium iodide was a grey-black etheral solution.

The 2-(2-acetoxy-5-acetylphenyl)2H-benzotriazole (2A5A) from Example 2 (40 g, 0.15 mole) was dissolved in dry tetrahydrofuran (200 ml), diluted with 150 ml of diethyl ether and was added to the Grignard reagent over a period of 30 minutes, keeping the etheral solution at gentle reflux. The solution changed color, and the reaction was stirred for an additional 1.5 hours, and was then treated with an aqueous solution of ammonium chloride (200 ml, 80 g, 1.5 mole). The organic layer was separated, the residue extracted twice with diethyl ether (200 ml), and the combined solutions were washed twice with water and dried over anhydrous sodium sulfate. The filtered solution was evaporated and gave 31 g (85%) of pale yellow crystals which were recrystallized from diethyl ether, m.p. 128°–129° C.

The calculated analysis for $C_{15}H_{15}N_3O_2$ was: C 66.89%, H 5.61%, N 15.60%.

The analysis found was C 66.55%, H 5.69%, N 15.23%.

EXAMPLE 4

Preparation of 2(2-hydroxy-5-isopropenylphenyl)2H-benzotriazole (2H5P)

The 2[2-hydroxy-5-(2-hydroxy-2-propyl)phenyl]2H-benzotriazole (2H5PR) of Example 3 was dehydrated using potassium hydrogen sulfate to produce 2(2-hydroxy-5-isopropenylphenyl)-2H-benzotriazole (2H5P).

2[2-hydroxy-5-(2-hydroxy-2-propyl)phenyl]2H-benzotriazole (2H5PR) (10 g, 0.04 mole) was mixed with freshly fused potassium hydrogen sulfate (1.0 g, 10 wt.%). The mixture was placed in the end bulb of a short path distillation apparatus (Kugelrohr) and slowly distilled at 160° C. and 0.05 mm Hg. White crystals were obtained in a yield of 8.8 g (88%). Recrystallization from n-hexane gave 2(2-hydroxy-5-isopropenylphenyl)2H-benzotriazole (2H5P) as a fine powder, m.p. 124°–124.5° C.

The compound was characterized by its ultraviolet spectrum: $\lambda_{max}=349$ nm (12,240 L/mole·cm), $\lambda_{max}=301$ nm (16,980 L/mole·cm), $\lambda_{max}=270$ nm (18,120 L/mole·cm); and its mass spectrum: m/e=251.

The analysis calculated for $C_{15}H_{13}N_3O$ was: C 70.87%, H 4.67%, N 16.71%.

The analysis found was: C 70.59%, H 4.52%, N 16.69%.

EXAMPLE 5

Preparation of 2[2-acetoxy-5-(1-hydroxyethyl)phenyl]2H-benzotriazole and 2(2-hydroxy-5-vinylphenyl)2H-benzotriazole The 2(2-acetoxy-5-acetylphenyl)2H-benzotriazole (2A5A) prepared in Example 2 is dissolved (1.0 g, 3.3 mmole) in 15 ml of diethyl ether and added dropwise into an Erlenmeyer flask containing sodium borohydride (0.13 g, 3.3 mmole) dissolved in 15 ml of ethanol. After one hour at room temperature, the reaction was terminated by adding a mixture of 30 ml of water and 5 ml of concentrated hydrochloric acid. Chloroform (30 ml) was used to extract the product from the aqueous solution, which, after drying and evaporation at 0.05 mm Hg gave 0.89 g (89%) of a colorless oil.

The $^1$H NMR spectrum showed it to be a mixture of 2[2-acetoxy-5-(1-hydroxyethyl)phenyl]2H-benzotriazole (2A5HE) and 2[2-hydroxy-5(1-hydroxyethyl)phenyl]2H-benzotriazole in a 1:3 ratio. The acetoxy derivative had a $\delta=2.32$ ppm

3H, singlet), and the hydroxy derivative showed δ=2.53 ppm (CH$_3$—C$\underline{\text{H}}$—OH, 3H singlet).

The crude oil was dehydrated by distilling the mixture with about 50 mg of potassium hydrogen sulfate in the presence of a few mg of picric acid. A mixture of 2-[2-acetoxy-5-vinylphenyl]2H-benzotriazole (2A5V) and 2(2-hydroxy-5-vinylphenyl)2H-benzotriazole (2H5V) distilled at 175° C. (0.075 mm Hg).

Hydrolysis of the 2A5V/2H5V Mixture

The mixture of 2-[2-acetoxy-5-vinylphenyl]2H-benzotriazole (2A5V) and 2(2-hydroxy-5-vinylphenyl)2H-benzotriazole (2H5V) was dissolved in methanol (25 ml), saturated aqueous sodium bicarbonate (15 ml) was added and the mixture was stirred overnight at room temperature. After acidification and extraction with chloroform (30 ml), crude 2(2-hydroxy-5-vinylphenyl)2H-benzotriazole (2H5V) was obtained, recrystallized from methanol:water (9:1) and gave pale yellow crystals, m.p. 98°–99° C.

The analysis calculated for $C_{14}H_{11}N_3O$ was C 70.87%, H 4.67%, N 17.71%, while the analysis found was C 70.95%, H 4.52%, N 17.69%.

The $^1$H NMR characterization was identical with that for 2H5V prepared by a different technique, *Makromol. Chem* infra. U.V. spectra: $\lambda_{max}$=350 nm (12,510 L/mole·cm), $\lambda_{max}$=301 nm (17,340 L/mole·cm), $\lambda_{max}$=269 nm (17,380 L/mole·cm).

Mass spectrum: m/e=237.

EXAMPLE 6

Homopolymerization Attempt Of 2(2-hydroxy-5-isopropenylphenyl)2H-benzotriazole (2H5P)

A 10 ml polymerization tube was charged with azobisisobutyronitrile (2 mg, 0.015 mmole), 2(2-hydroxy-5-isopropenylphenyl)2H-benzotriazole (2H5P) (1.26 g, 5 mmole), and toluene (2 ml). After three freeze-thaw cycles at 0.05 mm pressure to degas the homogeneous polymerization mixture, the tube was sealed and allowed to react for 3 days at 60° C. The tube was then opened and the solution was poured slowly into methanol (300 ml). No precipitation was observed initially, but upon cooling in ice/water a heavy white precipitate formd which after filtration gave 0.8 g of unchanged 2(2-hydroxy-5-isopropenylphenyl)2H-benzotriazole (2H5P) (m.p. 124° C.).

EXAMPLE 7

Copolymerization of 2(2-hydroxy-5-isopropenylphenyl)2H-benzotriazole (2H5P) With n-butyl acrylate A 20 ml polymerization tube was charged with azobisisobutyronitrile (3.9 mg, 0.03 mmole), 2(2-hydroxy-5-isopropenylphenyl)2H-benzotriazole (2H5P) (0.59 g, 2.3 mmole), purified by sublimation (115° C., 0.05 mm Hg) just before use, n-butyl acrylate (1.66 g, 13 mmole) and benzene (2 ml). The homogeneous mixture was degassed, sealed at 0.05 mm Hg, and placed in a constant temperature bath of 60° C. for 3 days.

The tube was then opened, the solution poured into methanol (250 ml) and the polylmer precipitated immediately as a rubbery mass. After two hours the methanol was decanted, the copolymer redissolved in benzene (3 ml) and precipitated by pouring the solution into methanol (100 ml). The reprecipitation was repeated, the copolymer dried, dissolved in benzene and finally isolated by freeze drying for 3 days at 0.05 mm Hg. The resultant product was poly(2H5P-co-BA) (1.56 g, 69% yield), with an inherent viscosity of 0.67 dL/g (0.5 g/dl in benzene, 25° C.).

The analysis calculated for $-\!(C_{15}H_{13}N_3O)_{\overline{0.08}}\!-\!(C_7H_{12}O_2)_{\overline{0.92}}$ is C 66.22%, H 8.72%, N 2.43%.

The analysis found for the polymer produced was C 66.27%, H 9.45%, N 2.58%.

EXAMPLE 8

Copolymerization of 2(2-hydroxy-5-isopropenylphenyl)2H-benzotriazole (2H5P) With Methyl Methacrylate A 20 ml polymerization tube was charged with azobisisobutyronitrile (20 mg, 0.146 mmole), 2-(2-hydroxy-5-isopropenylphenyl)2H-benzotriazole (2H5P) (2.82 g, 11.2 mmole), methyl methacrylate (6.42 g, 64.1 mmole) and toluene (8 ml).

The homogeneous mixture was degassed by three freeze-thaw cycles, sealed at 0.05 mm Hg, and placed in a constant temperature bath of 60° C. After 3 days, the tube was opened and the solution was poured into methanol (250 ml); the polymer precipitated immediately.

The suspension was allowed to settle for 2 hours, and was filtered and dried at 0.05 mm. The polymer was dissolved in chloroform (5 ml) and precipitated again into methanol (100 ml). After drying for one day at 72° C. and 0.05 mm Hg, poly (2H5P-co-MMA) was obtained in 16% yield (1.45 g), with an inherent viscosity of 0.13 dL/g (0.5 g/dl in toluene, 25° C.).

The analysis calculated for $-\!(C_{15}H_{13}N_3O)_{\overline{0.24}}(C_5H_8O_2)_{\overline{0.76}}$ is: C 65.21%; H 6.79%; N 7.39%.

The analysis found is: C 65.06%; H 6.85%; N 7.43%.

EXAMPLE 9

Copolymerizatin of 2(2-hydroxy-5-isopropenylphenyl)2H-benzotriazole (2H5P) With Styrene A 20 ml polymerization tube was charged with asobisisobutyronitrile (51 mg, 0.37 mmole), 2(2-hydroxy-5-isopropenylphenyl)2H-benzotriazole (2H5P) (2.82 g, 11 mmole) and styrene (6.6 g, 63 mmole). After three freeze-thaw cycles the homogeneous mixture was sealed at 0.05 mm Hg and placed in a constant temperature bath of 60° C. for 3 days.

After the tube was opened, the viscous solution was diluted with chloroform (10 ml) and poured into methanol (250 ml). The polymer precipitated was filtered and dried, redissolved in chloroform (10 ml) and precipitated by pouring the solution into methanol (100 ml). After drying for one day at 72° C. and 0.05 mm Hg, poly(2H5P-co-Styrene) (3.71 g, 39%) with an inherent viscosity of 0.29 dL/g (0.5 g/dl, toluene, 25%) was obtained.

The analysis calculated for $-\!(C_{15}H_{13}N_3O)_{\overline{0.175}}\!-\!(C_8H_8)_{\overline{0.825}}$ is C 84.37%, H 6.81%, N 5.60%, and the analysis found for the polymer produced was C 84.47%, H 6.95%, N 5.69%.

TABLE I

POLYMERIZATION OF 2(2-HYDROXY-5-ISOPROPENYLPHENYL)2H—BENZOTRIAZOLE
Polymerization Conditions: Initiator: Azobisisobutyronitrile, 0.2 mole %;
Temperature 60° C.; Time, 2.5 days; Sealed Tube; Pressure: 0.05 mm Hg

| 2H5P in g | 2H5P in mmole | Comonomer Type | Comonomer in g | Comonomer in mmole | Total Amount of Monomers in g | Total Amount of Monomers in mmole | Solvent type | Solvent Amt in ml | Polymer Yield in g | Polymer Yield in % | Plmr. Comp. 2H5P units | η inh Toluene dL/g |
|---|---|---|---|---|---|---|---|---|---|---|---|---|
| 1.26 | 5.0 | | | | 1.26 | 5 | Toluene | 2 | (a) | — | — | — |
| 2.82 | 11.2 | MMA | 6.42 | 64 | 9.24 | 75 | Toluene | 8 | 1.45 | 16 | 24 | 0.13 |
| 0.59 | 2.3 | BA | 1.66 | 13 | 2.25 | 15 | Benzene | 2 | 1.56 | 69 | 8 | 0.67 in benzene |
| 2.82 | 11.2 | ST | 6.63 | 64 | 9.45 | 75 | None | — | 3.71 | 39 | 17.4 | 0.29 |

(a) Monomer (2H5P) was recovered unchanged (m.p. 124° C.)
MMA = methyl methacrylate
BA = Butyl acrylate
ST = Styrene

We claim:
1. 2-(2-hydroxy-5-isopropenylphenyl)2H-benzotriazole.
2. The compound 2(2-hydroxy-5-isopropenylphenyl)2H-benzotriazole (2H5P) produced by azo coupling of o-nitrophenyl diazonium chloride with p-hydroxyacetophenone, subjecting the resulting isolated azo compound to reductive cyclization with zinc in the presence of sodium hydroxide at a temperature of about 50°–70° C., acidifying the resulting mixture so as to produce 2(2-hydroxy-5-acetylphenyl)2H-benzotriazole (2H5A), acetylating the isolated 2(2-hydroxy-5-acetylphenyl)2H-benzotriazole (2H5A) so as to produce 2(2-acetoxy-5-acetylphenyl)2H-benzotriazole (2A5A), methylating the isolated 2(2-acetoxy-5-acetylphenyl)2H-benzotriazole (2A5A) with a methyl Grignard reagent and dehydrating the isolated reaction product with potassium hydrogen sulfate so as to produce 2(2-hydroxy-5-isopropenylphenyl)2H-benzotriazole (2H5P).

* * * * *